(12) United States Patent
Wass et al.

(10) Patent No.: US 8,281,994 B1
(45) Date of Patent: Oct. 9, 2012

(54) BARCODE EMULATION IN MEDICAL DEVICE CONSUMPTION TRACKING SYSTEM

(75) Inventors: John S. Wass, Concord, MA (US); Jean-Claude Saghbini, Cambridge, MA (US)

(73) Assignee: WaveMark Inc., Littleton, MA (US)

( * ) Notice: Subject to any disclaimer, the term of this patent is extended or adjusted under 35 U.S.C. 154(b) by 40 days.

(21) Appl. No.: 11/765,950

(22) Filed: Jun. 20, 2007

Related U.S. Application Data

(60) Provisional application No. 60/805,413, filed on Jun. 21, 2006.

(51) Int. Cl.
    *G06F 19/00* (2011.01)
(52) U.S. Cl. ...................................... 235/385
(58) Field of Classification Search .............. 235/385; 340/10.1; 705/64, 65
    See application file for complete search history.

(56) References Cited

U.S. PATENT DOCUMENTS

| | | | | |
|---|---|---|---|---|
| 7,591,422 | B2* | 9/2009 | Maitin | 235/383 |
| 2002/0049650 | A1* | 4/2002 | Reff | 705/29 |
| 2002/0105424 | A1* | 8/2002 | Alicot et al. | 340/572.1 |
| 2004/0008123 | A1* | 1/2004 | Carrender et al. | 340/825.49 |
| 2004/0144842 | A1 | 7/2004 | Brignone et al. | |
| 2004/0196143 | A1* | 10/2004 | Crump et al. | 340/10.1 |
| 2005/0149226 | A1 | 7/2005 | Stevens et al. | |
| 2005/0149379 | A1 | 7/2005 | Cyr et al. | |
| 2005/0200453 | A1 | 9/2005 | Turner et al. | |
| 2005/0201450 | A1 | 9/2005 | Volpi et al. | |
| 2005/0280536 | A1 | 12/2005 | Hamilton et al. | |
| 2006/0082440 | A1 | 4/2006 | Glaser et al. | |
| 2006/0089918 | A1 | 4/2006 | Avanzi et al. | |
| 2007/0156281 | A1* | 7/2007 | Leung et al. | 700/225 |
| 2007/0285242 | A1* | 12/2007 | Higham | 340/572.1 |

* cited by examiner

*Primary Examiner* — Thien M Le
*Assistant Examiner* — Sonji Johnson
(74) *Attorney, Agent, or Firm* — Houston & Associates LLP

(57) ABSTRACT

An interface system for providing product identifier data to a legacy system for a unit tracking system comprises a reader for reading unit tracking information for items. The unit tracking information uniquely identifies each of the items. In one example, this unit tracking information is an RFID serial number. Then, a translator looks up universal product numbers associated with the items with which the unit tracking number is associated. The translator passes the universal product number to the legacy system.

21 Claims, 3 Drawing Sheets

BARCODE EMULATION IN MEDICAL DEVICE CONSUMPTION TRACKING SYSTEM

RELATED APPLICATIONS

This application claims the benefit under 35 USC 119(e) of U.S. Provisional Application No. 60/805,413, filed on Jun. 21, 2006, which is incorporated herein by reference in its entirety.

BACKGROUND OF THE INVENTION

Radio Frequency Identification (RFID) systems have been proposed for the tracking of medical supplies in hospitals. Such systems typically involve one or more readers and many RFID tags, each of which is associated with, such as attached to, items being monitored or tracked. In the case of medicaments, single-use medical devices, and implantable medical devices, RFID tags are typically affixed to or made part of the medicament container, e.g., medicine bottle, or medical device container, e.g., disposable packaging for the stent or orthopedic implant.

RFID tags take the form of integrated circuits, with associated antennas, that encode unique serial numbers. The reader is generally in a fixed location or mobile with an operator, and items with RFID tags are detected when they enter or leave the electromagnetic field of the reader. For example, RFID readers are often placed at multiple distributed locations associated with a supply chain in order to monitor the items as they passes through manufacturing, transportation, distribution, to consumption. Each reader captures the RFID tag serial numbers of each item as it enters the reader's interrogation field, and data collected from all readers facilitate item tracking over time, through the chain.

Tracking using RFID-based systems and also tradition systems based on bar code readers generally deteriorates as the items being tracked approach the time and place of consumption, e.g., use, implantation, exhaustion, or disposal. It is therefore difficult to trace a particular item's full history. Part of the problem is that the individuals that are directly involved with the consumption of the item, e.g., medical care professionals, are usually, and justifiably, more concerned with medical care delivery than the integrity of the supply chain data.

For example, the most common practice in accounting for product use and disposition is based on manual data entry, sometimes assisted by barcode scans to obtain a product identifier such as a stock keeping unit (SKU) number or the universal product number (UPN) of the item. These manual procedures record the usage and disposition of supplies. The data entry often must be performed under time constraints that do not allow verification of the data entered, however. Consequently, error rates can be high and data quality is often poor.

Moreover, often responsibilities concerning reporting of item consumption may be made more difficult or confusing because of the presence of legacy systems, which may or may not be compatible with the RFID tracking systems. Thus, it is not uncommon that the same event must be reported to multiple supply chain systems due to incompatibility between those systems.

Further, these legacy tracking systems often do not track each item uniquely. The reason is that the systems usually track based on the barcode scanned UPN of the item. The product identifier, e.g., UPN) is only unique to the type of item and maybe a lot or batch. The UPN does not uniquely identify each item. In contrast, RFID tags each have unique numbers. Thus, when associated with an item, that item can be uniquely tracked all the way to the point of consumption, and possibly beyond. However, this per item tracking is inconsistent with the legacy systems that only track via a product identifier, for example.

SUMMARY OF THE INVENTION

The present invention concerns interfacing between legacy systems, such as systems that track items via product identifiers, with tracking systems that enable the tracking of each unique item through the supply chain.

In general, according to one aspect, the invention features an interface system for providing product identifier data to a legacy system, or system that is product identifier based, from a unit tracking system. The system comprises a reader for reading unit tracking information for items. The unit tracking information uniquely identifies each of the items. In one example, this unit tracking information is an RFID serial number. Then, a translator looks up product identifier data associated with the items with which the unit tracking number is associated. The translator passes the product identifier to the system that uses such product identifiers.

In one example, the legacy system tracks consumption of items in medical procedures, such a catheterization laboratories. The translator passes product identifier data to the legacy system by emulating an input device for the product identifier data, such as a bar code reader input device.

Converting the RFID serial numbers to the product identifier data is performed locally in the translator in one embodiment. In another embodiment, the translator accesses a remote database. Periodically, the translator may update its internal database in order to minimize the number of network transactions and also increase the speed of its operation.

In general, according to another aspect, the invention features a method for updating the legacy system with product identifier data from a unit tracking system. The method comprises reading unit tracking information from items, the unit tracking information uniquely identifying each of the items. The product identifier data associated with the items are looked up using the unit tracking numbers. This product identifier data are then passed to the legacy system or system that uses the product identifier data rather than unit tracking data.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Example Hospital Tracking System

Figure 1:
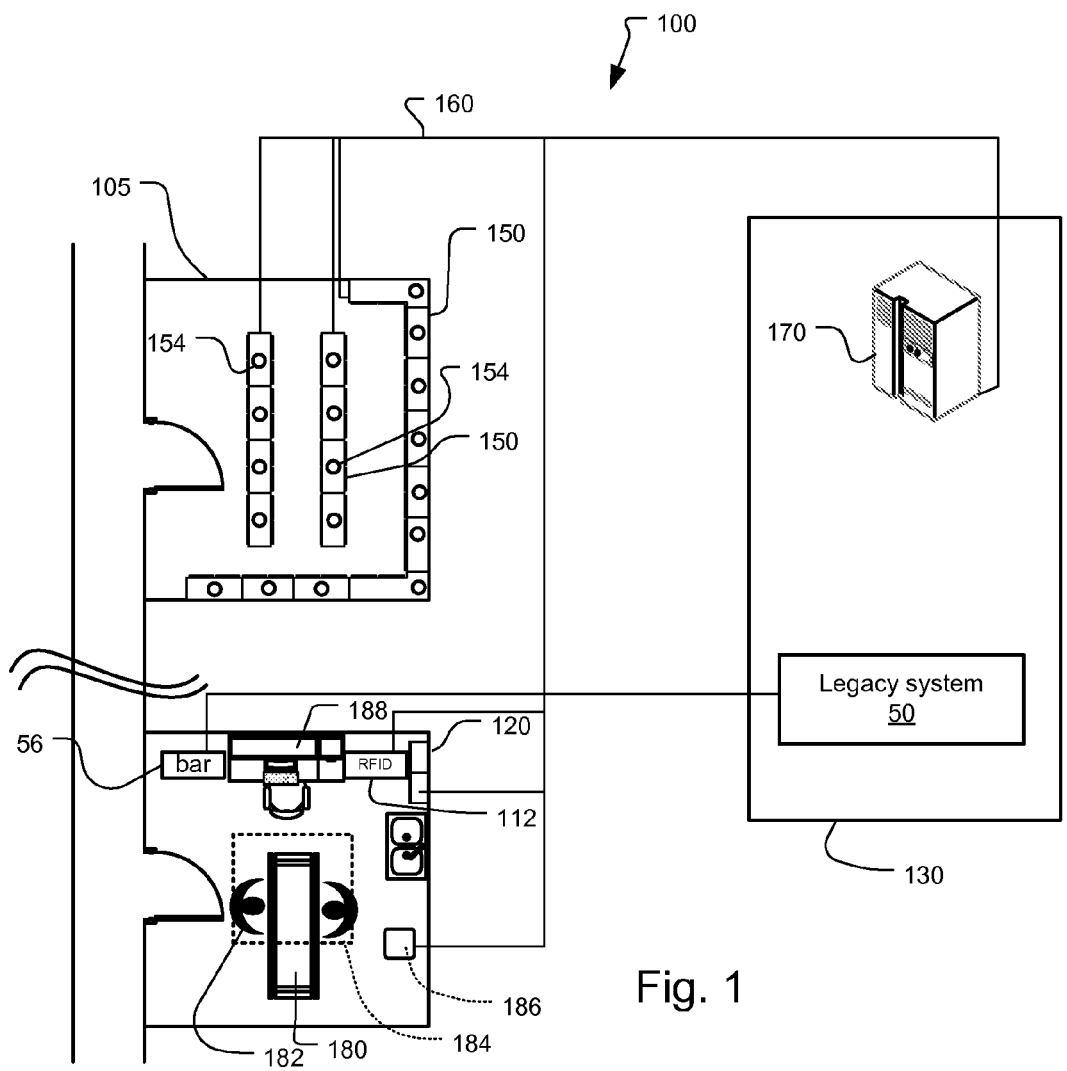
FIG. 1 is a schematic diagram illustrating a medical item tracking system with a legacy system according to the present invention.

FIG. 1 shows an exemplary inventory tracking system 100. This example is RFID-based, monitoring inventory levels in store rooms and storage cabinets. The system is more completely described in U.S. patent application Ser. No. 11/383,422, filed on May 15, 2006, entitled RFID Medical Supplies Consumption Monitoring System and Method, by Wass et al., which is incorporated herein in its entirety by this reference.

The tracking system 100 is described in the context of a hospital or other medical care delivery facility such as a long-term care facility, doctors' office, animal hospital, and other institution that delivers medical care including state institutions and prisons.

The hospital or other medical care facility generally comprises a medical supply room 105 that is devoted to housing supplies including medical items, a procedure room 120 where the medical items are consumed, such as used or implanted in patients, and a local or off-site server or network area 130 that houses the information technology infrastructure for the facility.

In more detail, the medical supply room 105 in the example comprises a number of medical supply cabinets or other storage units 150. In the preferred embodiment, each of the medical supply cabinets 150 is a radio frequency identification (RFID) cabinet that includes an associated RFID reader 154. These medical supply room/cabinet readers 154 are capable of detecting and reading RFID tags of medical items stored in the cabinets 150.

The RFID cabinet readers 154 of the medical supply location 105 are networked onto a communications network 160. Specifically, the readers 154 communicate via the communications network 160, such as a local area network (LAN), to an inventory management system 170. In this way, the inventory management system 170 is able to track the presence of the medical items in the storage cabinets 150 in real-time without intervention by staff. Thus, no action is required by the hospital personnel in order to enable the inventory management system 172 to detect the presence of the medical items. Further, there is no staff intervention required when items are removed since the periodic scan of the cabinet contents by the readers 154 detects removal, which is then reported to the inventory management system 170. Finally, this inventory tracking system, being RFID-based, is able to track each item inventory, uniquely, according to the unique serial number encoded in each RFID tag.

Most often the medical items are removed from the medical supply location 105 when they are going to be used in the treatment of patients at the facility. Medical procedures requiring the items often are performed in the procedure rooms 120. In some examples, this room 120 is simply a patient examining room for simple procedures such as injections. In other examples, the procedure room 120 is an operating room, a diagnostic or monitoring room, or a dedicated-use room such as a catheterization laboratory (cathlab), or control room for a cathlab. In other examples, the procedures are performed operating rooms, interventional radiology rooms, electro-physiology rooms and/or for orthopedics.

The procedure room 120 has one or more associated procedure room RFID readers. In the illustrated example, the procedure room has an RFID reader associated with a refuse container 186 system and/or an RFID reader 112 associated with a workstation 188. These RFID readers are used to detect the usage of the medical items in the context of the procedure being performed by medical professionals 182, 184 on a patient on table 180.

The RFID inventory management system 170 usually functions in cooperation with and in parallel to a legacy system 50. Often, this legacy system 50 is the system that is designed to accept barcode input from bar code readers 56, also distributed around the facility, often including the procedure room 120. The legacy system differs from the RFID inventory management system insofar as the legacy system 50 tracks based on product identifier data, which only identifies the type of product and is not unique to each item.

Most often, the legacy systems 50 are notable in that they use product identifier data such as stock keeping unit (SKU) numbers or codes. Specific examples include Universal Product Code (UPC), European Article Number (EAN), and Global Trade Item Number (GTIN). These codes, encoded in bar codes or other machine readable labels, for example, only provide the information concerning the item type and possibly a lot or batch number. In contrast, they are not unique serial numbers that uniquely identify each item, but instead only identify the item type.

Unique identification and tracking of individual items may not be cost effective or necessary for inexpensive items. However, for high value and/or small items, susceptible to loss or theft, such per-item tracking can be very cost effective.

Figure 2:
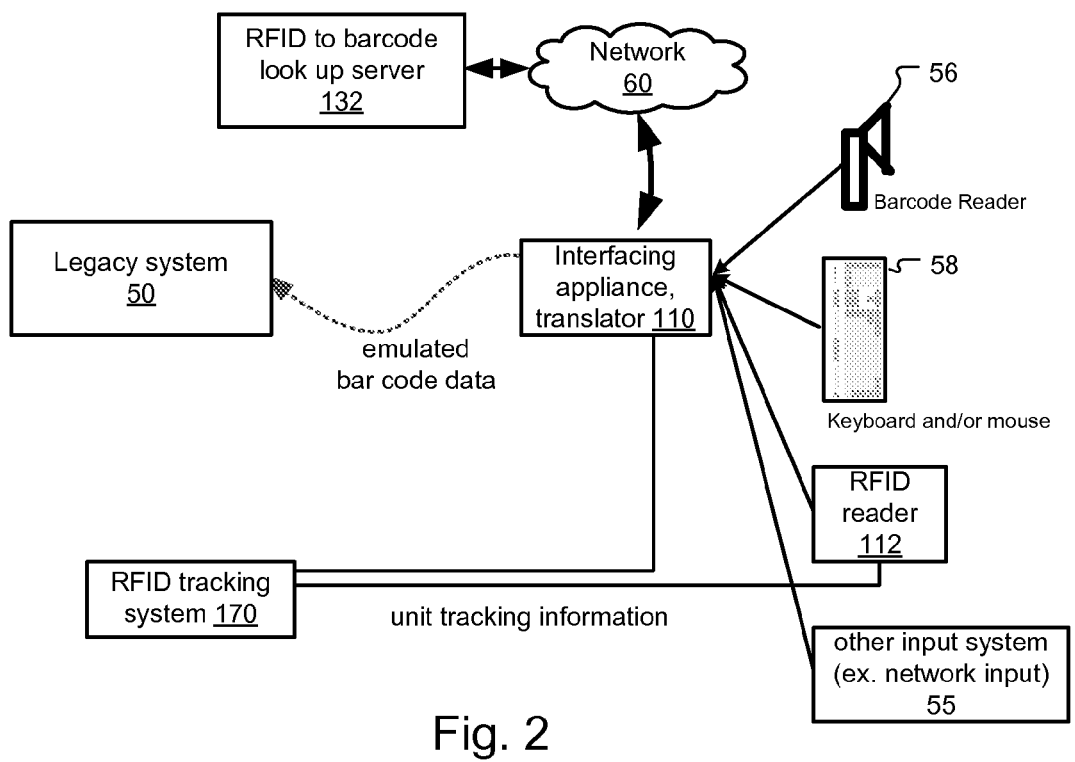
FIG. 2 is a schematic block diagram illustrating the relationship between the RFID tracking system, legacy system, and the interfacing appliance/translator 110 according to the present invention.

FIG. 2 shows the relationship between the interfacing appliance 110 and the legacy system 50 and the RFID tracking system 170. Generally, interfacing appliance 110 enables information obtained from RFID tag reads to be used to update legacy systems that accept barcode data or similar machine readable information.

By way of background, items are tracked through inventory using a number of different modalities in some situations. As described previously in FIG. 1, RFID readers 112 are used in some examples that collect inventory information for the RFID tracking system 170 without user intervention or by using a hand-held RFID reader in tracking. In other examples, other input systems are provided 55. In one example, a keyboard 58 is used that allows user to manually enter SKU or UPN numbers. In a common example, a bar code reader 56 is used. These existing legacy input devices such as a bar code reader 56 and the keyboard 58 are used to provide consumption information to the legacy system 50, which is often the supply chain, billing and/or existing inventory tracking system for the institution, such as the hospital.

Since this legacy system 50 coexists with the RFID tracking system 170, it is important to, on one hand, make information coherent between their respective databases. Secondly, it is important to minimize the burden on the users in terms of having to enter information into both the legacy system 50 and the RFID tracking system 170 to report an inventory event such as consumption of an inventory item in a procedure. To handle the situation, an interfacing appliance/translator 110 is used. This appliance 110 receives bar code input from a bar code reader 56 or other device that provide product identifier data. In a preferred embodiment also receives input from an RFID reader 112, or other device that provides unit tracking data. This can be the same RFID reader that is used by the RFID tracking system.

In some examples, a single interface appliance 110 accommodates multiple inputs that then get transformed into a barcode emulation input to the legacy system 50 in one example. One input is a direct input from the bar code reader 56. The barcode data that gets read from the barcode reader gets passed through to the legacy system 50, or gets manipulated, or transformed (used as a lookup) to send another set of data via the barcode emulation. In another example, however, the bar code reader 56 directly reports the decoded bar code data to the legacy system.

The input can also be from the keyboard/mouse 58, whereby a user input with a keyboard or mouse results in data being barcode emulated out of the appliance and into the legacy system 50. RFID reader 112 is another input. In still another example, other inputs 55, such as network input, trigger the interface appliance 110 to send the barcode emulation data to the legacy system 50.

In order to provide information to the legacy system 50 which does not have access to the RFID reader 112 and does not have per-item tracking, the interfacing appliance/translator 110 must convert the read RFID serial number from the RFID reader 112 into product identifier data, such as a SKU code, UPN for example. In this embodiment the interfacing appliance 110 accesses either a local internal database that maps the RFID number to the particular type of the item or accesses an RFID to bar code lookup server 132 preferably over a network 60, possibly including a public network. This translation, performed by the interfacing appliance 110, returns the SKU or UPN number, for example, that is used by the legacy system 50. Then the interfacing appliance 110 transmits in one embodiment, emulated bar code data to the legacy system 50 to thereby enable the legacy system 50 to update its databases concerning the consumption, for example, of the item. Nevertheless, from the standpoint of the operator/medical care delivery personnel, only a single transaction was required.

Figure 3:
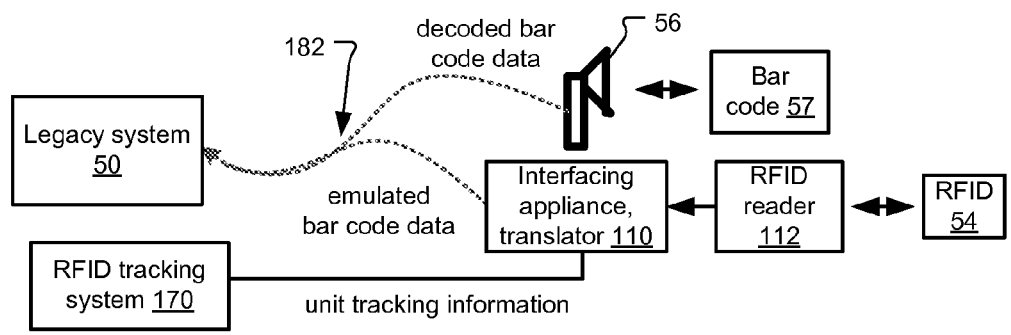
FIG. 3 illustrates one implementation of the connection between the RFID interfacing appliance/translator and the legacy system.

FIG. 3 shows one implementation of the interfacing appliance 110 that enables information obtained from RFID tag reads of an RFID tag 54 to be used to update legacy systems 50 that accept barcode data or similar machine readable information from typical barcodes 57. Further, the interfacing appliance 110 directly sends the RFID serial number to the RFID system 170. Thus a single transaction, reading of an RFID, allows the interfacing appliance to update both the RFID tracking system 170 and the legacy system 50.

The interface appliance or translator 110 emulates barcode data into the legacy system 50, which is designed to accept barcode input. Thus, it can either replace the existing barcode reader 56 or coexist with it. In the case of coexistence, the user has the ability to enter the data either using the barcode reader 56 or via the emulation from the interface appliance 110 from the RFID reader 112 and RFID 54. Two ways are supported for the physical connection between the system: a Y-splitter 182, in which the barcode reader and the interface appliance feed into a single port input into the legacy system 50. As result, items that only have a bar code 57 but no RFID 54 can still be scanned by the bar code reader 56 and the transaction reported to the legacy system 50 by virtue of the interfacing appliance 110 simply passing the bar code data to the legacy system 50. Thus, in this operation, the interfacing appliance is transparent to the legacy system 50.

Figure 4:
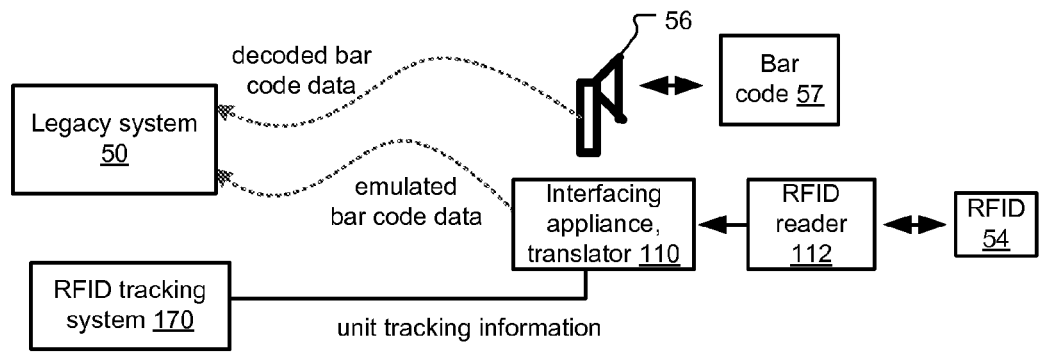
FIG. 4 shows a second implementation of the connection between the RFID interfacing appliance/translator and the legacy system.

As shown in FIG. 4, the interfacing appliance can alternatively be connected to a separate port into the legacy system 50, one for the barcode reader 56, and one for the interface appliance 110. In either case, the legacy system receives the bar code data associated with an item either: 1) from scan of bar code 57 by reader 56, or 2) by emulation using the RFID 54 read by reader 112, with the interfacing appliance 110 looking up the appropriate bar code data that is then emulated for the legacy system 50.

Specific Cathlab Integration Examples:

In one embodiment, items that are RFID tagged are only scanned by the RFID reader 112. From there, both RFID tracking system 170 and the legacy system 50 are updated with the usage or consumption information. The update of the legacy system 50 cannot be accomplished directly, however. A reverse-lookup is performed to get the barcode information for the product based on its RFID tag. These lookup data are generated directly by the interfacing appliance by reference to an internal database or sent to the interface appliance 110 from the server 132 over the network 60.

In more detail, Camtronics Medical Systems, Ltd has a hemodynamic system that is designed for use in the control room of the hospital catheterization laboratory (cathlab). This specific product is named Physiolog version 3.3, which will be updated to Heartsuite 6.10.

In typical operation, when an item is used during a procedure, the barcode of the item is scanned into the hemodynamic system, Physiolog for example, to reflect its association with a patient and typically the consumption of the item in the medical procedure, for example.

Physiolog 3.3 runs on a server that is installed in the control room. A barcode reader is attached to the server via a serial connection.

The barcode reader is programmed to send a data payload that is captured and interpreted as a used item barcode.

When interfacing to Physiolog 3.3, the translator 110 generally emulates a keyboard output over universal serial bus (USB). When an RFID tagged product 54 is scanned by the RFID reader 112, the RFID data are extracted and provided to the translator 110. The translator 110 performs a lookup. In one example, the lookup is local to a pre-loaded database of the translator 110. If this lookup fails, then the translator 110 accesses a master database on a remote server 132, over network 60, possibly including a public network.

The lookup process results in the retrieval of the universal product number (UPN) for the RFID tagged item, since the lookup maps RFID codes to items and the UPN for those items.

The translator 110 sends the barcode UPN over the USB output as keyboard emulation. The data are received by control room server 50 of the Physiolog legacy system. In the preferred embodiment, the translator 110 also sends the RFID data to the RFID tracking system 170.

In Heartsuite the barcode reader 52 is also programmed to send a scanned barcode. The data are sent as characters over the serial cable COM2. The Heartsuite 6.10 program on the control room server 50 listens for serial input on COM2 captures it and interprets it as a used item barcode.

As a result, the translator 110 here outputs serial data using the specified protocol. Thus, an RFID tagged product is scanned by the RFID reader 112. The lookup is done (locally through a pre-loaded database, and/or remotely from the main lookup server 132) and the UPN barcode is retrieved and sent over a serial cable to the Heartsuite system.

Given that the Heartsuite software is only listening on COM2, and given that the RFID reader 112 needs to coexist with the barcode reader 52 since not all products are RFID tagged, this means that both the output of the barcode reader 52 as well as the output of the RFID reader 112 have to come in over COM2. This can be done in one of two configurations: 1) the use of a serial splitter (FIG. 3); or 2) have the barcode reader 56 function as an input to the interfacing appliance/translator 110. In this second configuration, the interfacing appliance 110 has two serial ports. One serial port is attached to the legacy system 50, and the other to the barcode reader 56. All data coming from the barcode reader 56 are just passed through via the second serial connection to the legacy system 50. The RFID-barcode translated data are also sent via this serial cable.

In other implementations, the interfacing appliance 110 translates to the MacLab medical system sold by General Electric Corporation. In other example, the appliance provides data to a manufacturer's shipping system. Such systems are being used currently by the shipping staff in the distribution center to read barcode data from the products to be shipped.

While this invention has been particularly shown and described with references to preferred embodiments thereof, it will be understood by those skilled in the art that various changes in form and details may be made therein without departing from the scope of the invention encompassed by the appended claims.

What is claimed is:

1. An interface system for providing bar code data to a legacy system, which tracks via bar code data, from a unit tracking system, the system comprising:
    a reader for reading unit tracking information of the unit tracking system from items, the unit tracking information uniquely identifying each of the items individually in the unit tracking system; and
    a translator for looking up the bar code data associated with the items using the unit tracking information in a database that maps the unit tracking information to the bar code data, the bar code data indicating a type of the item but not identifying each item individually, the translator passing the bar code data derived from the database to the legacy system by emulating a bar code reader input device of the legacy system for the bar code data, wherein the legacy system only accepts bar code data pertaining to the items.

2. An interface system as claimed in claim 1, wherein the unit tracking system associates a unique number with each of the tracked items.

3. An interface system as claimed in claim 1, wherein the reader is a RFID reader.

4. An interface system as claimed in claim 1, further comprising a lookup server maintaining the database, the translator passing the unit tracking information to the lookup server, which returns corresponding bar code data for the items tagged with the unit tracking information.

5. An interface system as claimed in claim 4, wherein the lookup server is remote from the translator.

6. An interface system as claimed in claim 1, wherein the translator maintains the database that maps the unit tracking information to corresponding bar code data for the items tagged with the unit tracking information.

7. An interface system as claimed in claim 1, wherein the bar code data are numbers encoded by bar codes located on the items.

8. An interface system as claimed in claim 1, wherein the bar code data are stock keeping unit numbers encoded by bar codes located on the items.

9. An interface system as claimed in claim 1, wherein the translator emulates the bar code reader input device over a serial connection.

10. A system that provides bar code data to a legacy system, which tracks consumption of medical items in medical procedures via bar code data, from a unit tracking system, the system comprising:
    a medical procedure room in which the medical procedures are performed on patients;
    a reader, in the medical procedure room, for reading unit tracking information of the unit tracking system from medical items to be used in the medical procedures, the unit tracking information uniquely identifying each of the medical items; and
    a translator for looking up the bar code data associated with the medical items using the unit tracking information in a database that maps the unit tracking information to the bar code data, with which the unit tracking information is associated, the translator passing the bar code data derived from the database to the legacy system by emulating a bar code reader input device of the legacy system, wherein the legacy system only accepts bar code data pertaining to the medical items.

11. A system as claimed in claim 10, wherein the legacy system tracks consumption of items in procedures performed in catheterization laboratories.

12. A system as claimed in claim 10, wherein the translator passes the bar code data to the legacy system by connecting to a serial port of the legacy system in the medical procedures room for the bar code data.

13. A method for updating a legacy system with bar code data with a unit tracking system, the method comprising:
    reading unit tracking information from items, the unit tracking information uniquely identifying each of the items individually in the unit tracking system;
    looking up bar code data associated with the items, with which the unit tracking information is associated in a database that maps the unit tracking information to the bar code data, the bar code data indicating a type of the item but not identifying each item individually; and
    passing the bar code data derived from the database to the legacy system by emulating an input device of the legacy system for the bar code data, wherein the legacy system only accepts bar code data pertaining to the items.

14. A method as claimed in claim 13, wherein the unit tracking system associates a unique number with each of the tracked items.

15. A method as claimed in claim 13, further comprising reading an RFID to obtain the unit tracking information.

16. A method as claimed in claim 13, wherein the step of passing the bar code data comprises passing the bar code data to the legacy system by emulating a bar code reader input device.

17. A method as claimed in claim 13, further comprising passing the unit tracking information to a lookup server that maintains the database, which returns corresponding bar code data for the items tagged with the unit tracking information.

18. A method as claimed in claim 17, wherein the lookup server is remote from the translator.

19. A method that tracks consumption of medical items in medical procedures, comprising:
    performing the medical procedures on patients in a medical procedures room using the medical items;
    reading unit tracking information from the medical items in the medical procedures room, the unit tracking information uniquely identifying each of the medical items individually in a unit tracking system;
    looking up bar code data associated with the medical items, with which the unit tracking information is associated in a database that maps the unit tracking information to the bar code data, the bar code data indicating a type of the medical item but not identifying each medical item individually; and
    passing the bar code data to a legacy system derived from the database.

20. A method as claimed in claim 19, wherein the legacy system tracks consumption of medical items in procedures performed in catheterization laboratories.

21. A method as claimed in claim 19, wherein the step of passing the bar code data to the legacy system comprises emulating a bar code reader input device of the legacy system in the medical procedures room for the bar code data.

* * * * *